(12) United States Patent
Baura et al.

(10) Patent No.: US 6,636,754 B1
(45) Date of Patent: Oct. 21, 2003

(54) APPARATUS AND METHOD FOR DETERMINING CARDIAC OUTPUT IN A LIVING SUBJECT

(75) Inventors: Gail D. Baura, San Diego, CA (US); James O. Elf, San Diego, CA (US)

(73) Assignee: Cardiodynamics International Corporation, San Diego, CA (US)

(*) Notice: Subject to any disclaimer, the term of this patent is extended or adjusted under 35 U.S.C. 154(b) by 41 days.

(21) Appl. No.: 09/613,183

(22) Filed: Jul. 10, 2000

(51) Int. Cl.$^7$ ............................................. A61B 5/0908
(52) U.S. Cl. ........................ 600/393; 600/372; 600/382
(58) Field of Search ................................. 600/372, 382, 600/393, 394, 509; 607/28, 152, 149

(56) References Cited

U.S. PATENT DOCUMENTS

| | | | |
|---|---|---|---|
| RE30,101 E | | 9/1979 | Kubicek et al. |
| 5,184,620 A | * | 2/1993 | Cudahy et al. |
| 5,895,298 A | | 4/1999 | Faupel et al. |
| 6,141,575 A | * | 10/2000 | Price |

OTHER PUBLICATIONS

G. W. N. Dalzell, et al., "Initial Experience with a Microprocessor Controlled Current Based Defibrillator," University of Ulster, Jordanstown, and Regional Medical Cardiology Centre, Royal Victoria Hospital, Belfast, Ireland, pp. 502–505, Feb. 2, 1989.

B. Bo Sramek, MSEE, "Hemodynamic and Pump–Performance Monitoring by Electrical Bioimpedance," Problems in Respiratory Care, vol. 2, No.2, pp. 274–290, Apr./Jun. 1989.

G. D. Baura, Ph.D., et al., "Intra–Sensor Spacing and Sensor Placement Variability on Impedance Cardiography (ICG) Parameters," CDIC Technical Report #TR–048, consisting of 2 pages, Jul. 26, 2000.

ConMed Corporation Positrace ECG Electrode (Exhibit "A" consisting of five pages), 6/98.

Wantagh, Incorporated, "Noninvasive Continuous Hemodynamic Patient Monitoring System – Operator's Manual," Title page, plus pp. 1–42 (date unknown).

(List continued on next page.)

Primary Examiner—Scott M. Getzow
(74) Attorney, Agent, or Firm—Gazdzinski & Associates

(57) ABSTRACT

An improved apparatus and method for determining the cardiac output of a living subject. The improved apparatus generally comprises one or more electrode assemblies or patches affixed to the skin of the subject in the vicinity of the thoracic cavity. The terminals of each electrode patch are in contact with an electrolytic gel, and are spaced a predetermined distance from one another within the patch. This predetermined spacing allows for more consistent measurements, and also allows for the detection of a loss of electrical continuity between the terminals of the patch and their associated electrical connectors in the clinical environment. The method generally comprises generating and passing a stimulation current through the terminals and the thoracic cavity of the subject, and measuring the impedance as a function of time. This impedance is used to determine cardiac muscle stroke volume, which is then used in conjunction with the subject's cardiac rate (also detected via the electrode patches) to determine cardiac output. A method of detecting a loss of electrical continuity in one or more of the terminals of the electrode patch is also disclosed.

32 Claims, 11 Drawing Sheets

OTHER PUBLICATIONS

Wantagh, Incorporated, "Noninvasive Continuous Hemodynamic Monitoring," pp. 1–4 (date unknown).

Lead–Lok, Inc., (Aug. 8, 1998), Final Production Specifications consisting of two (2) pages.

Sorba Medical Systems – product literature entitled "Transthoracic Electrical Bioimpedance R–wave Triggered Ensemble" Averaging consisting of four (4) pages.

Sorba Medical Systems – product literature regarding the CIC–1000™–consisting of two (2) pages.

Sorba Medical Systems – product literature regarding the Steorra™ impedance cardiograph –consisting of three (3) pages.

W. G. Kubicek, Ph.D., et al., "Development and Evaluation of an Impedance Cardiac Output System", Acrospace Medicine, pp. 1208–1212, Dec. 1966.

Jan Nybor, Sc.D., M.D., et al., "Electrical Impedance Plethysmography", Circulation, vol. II, pp. 811–821, Dec., 1950.

* cited by examiner

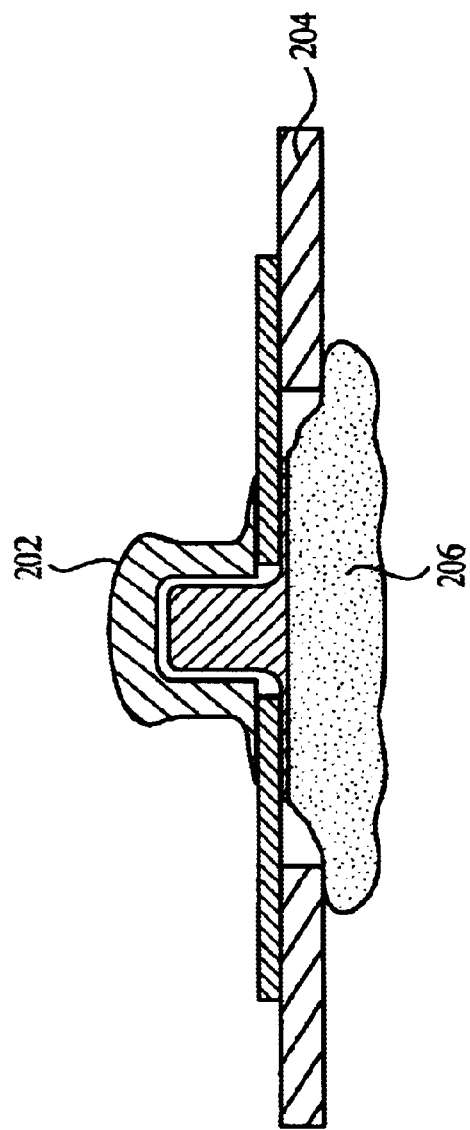
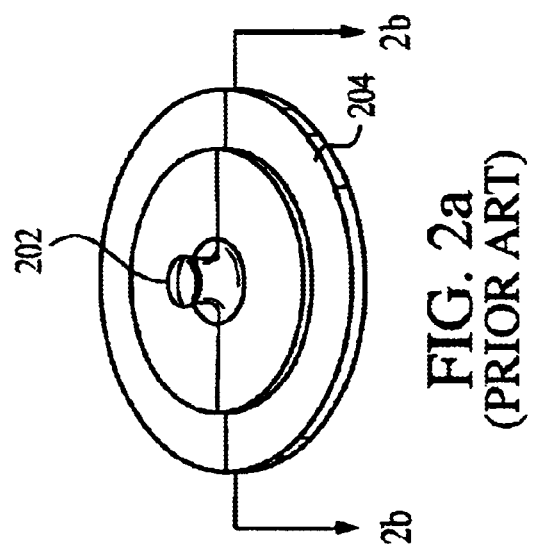
FIG. 2b (PRIOR ART)
FIG. 2a (PRIOR ART)

(PART 1 OF 2)

(PART 2 OF 2)

APPARATUS AND METHOD FOR DETERMINING CARDIAC OUTPUT IN A LIVING SUBJECT

This application is a Request for Continued Examination (RCE) of U.S. patent application Ser. No. 09/613,183 of the same title filed Jul. 10, 2000, which is incorporated herein by reference in its entirety.

BACKGROUND OF THE INVENTION

1. Field of the Invention

The present invention relates generally to the field of biomedical analysis, and particularly to an apparatus and method for non-invasively determining the cardiac output in a living subject using impedance cardiography.

2. Description of Related Technology

Noninvasive estimates of cardiac output (CO) can be obtained using impedance cardiography. Strictly speaking, impedance cardiography, also known as thoracic bioimpedance or impedance plethysmography, is used to measure the stroke volume of the heart. As shown in Eq. (1), when the stroke volume is multiplied by heart rate, cardiac output is obtained.

$$CO = \text{stroke volume} \times \text{heart rate}. \quad (1)$$

The heart rate is obtained from an electrocardiogram. The basic method of correlating thoracic, or chest cavity, impedance, $Z_T(t)$, with stroke volume was developed by Kubicek, et al. at the University of Minnesota for use by NASA. See, e.g., U.S. Reissue Patent No. 30,101 entitled "Impedance plethysmograph" issued Sep. 25, 1979, which is incorporated herein by reference in its entirety. The method generally comprises modeling the thoracic impedance $Z_T(t)$ as a constant impedance, $Z_o$, and time-varying impedance, $\Delta Z(t)$, as illustrated schematically in FIG. 1. The time-varying impedance is measured by way of an impedance waveform derived from electrodes placed on various locations of the subject's thorax; changes in the impedance over time can then be related to the change in fluidic volume (i.e., stroke volume), and ultimately cardiac output via Eqn. (1) above.

Despite their general utility, prior art impedance cardiography techniques such as those developed by Kubicek, et al. have suffered from certain disabilities. First, the distance (and orientation) between the terminals of the electrodes of the cardiography device which are placed on the skin of the subject is highly variable; this variability introduces error into the impedance measurements. Specifically, under the prior art approaches, individual electrodes 200 such as that shown in FIGS. 2a and 2b, which typically include a button "snap" type connector 202, compliant substrate 204, and gel electrolyte 206 are affixed to the skin of the subject at locations determined by the clinician. Since there is no direct physical coupling between the individual electrodes, their placement is somewhat arbitrary, both with respect to the subject and with respect to each other. Hence, two measurements of the same subject by the same clinician may produce different results, dependent at least in part on the clinician's choice of placement location for the electrodes. It has further been shown that with respect to impedance cardiography measurements, certain values of electrode spacing yield better results than other values.

Additionally, as the subject moves, contorts, and/or respirates during the measurement, the relative orientation and position of the individual electrodes may vary significantly. Electrodes utilizing a weak adhesive may also be displaced laterally to a different location on the skin through subject movement, tension on the electrical leads connected to the electrodes, or even incidental contact. This so-called "motion artifact" can also reflect itself as reduced accuracy of the cardiac output measurements obtained using the impedance cardiography device.

A second disability associated with prior art impedance cardiography techniques relates to the detection of a degraded electrical connection or loss of electrical continuity between the terminals of the electrode and the electrical leads used to connect thereto. Specifically, as the subject moves or sweats during the measurement, the electrolyte of the electrode may lose contact with the skin, and/or the electrical leads may become partially or completely disconnected from the terminals of the electrode. These conditions result at best in a degraded signal, and at worst in a measurement which is not representative of the actual physiological condition of the subject.

Another significant consideration in the use of electrodes as part of impedance cardiographic measurements is the downward or normal pressure applied to the subject in applying the electrode to the skin, and connecting the electrical leads to the electrode. It is desirable to minimize the amount of pressure needed to securely affix the electrode to the subject's skin (as well as engage the electrical lead to the electrode), especially in subjects whose skin has been compromised by way of surgery or other injury, since significant pressure can result in pain, and reopening of wounds.

Based on the foregoing, there is a need for an improved apparatus and method for measuring cardiac output in a living subject. Such improved apparatus and method ideally would allow the clinician to repeatedly and consistently place the electrodes at the optimal locations. Additionally, such an improved apparatus and method would also permit the detection of degraded electrical continuity between the electrode terminal and skin, or the electrode terminal and electrical leads of the measurement system, and be adapted to minimize the normal pressure on the subject's tissue when applying the electrodes and electrical leads.

SUMMARY OF THE INVENTION

The present invention satisfies the aforementioned needs by providing an improved method and apparatus for measuring the cardiac output of a living subject.

In a first aspect of the invention, an improved apparatus for determining the cardiac output of a living subject is disclosed. The apparatus generally comprises: a plurality of electrode assemblies having a plurality of terminals, at least two of the plurality of terminals being spaced from one another by a predetermined distance; a current source capable of generating a substantially constant current; a plurality of electrical leads connecting the current source with individual ones of the terminals of the electrode assemblies, a circuit for measuring the difference in voltage at the terminals resulting from the flow of current through the subject and the terminals; and a circuit for measuring ECG potentials from at least one of the electrode assemblies. In one exemplary embodiment, the subject is a human being. Cardiac stroke volume is measured by applying a constant current to the stimulation electrodes, measuring the resulting voltage differential, and determining the stroke volume from the measured voltage and a predetermined relationship describing intra-thoracic impedance.

In a second aspect of the invention, an improved cardiac electrode apparatus is disclosed. The apparatus generally comprises: a substrate having a plurality of apertures formed therein, at least two of the apertures being formed a predetermined distance apart; a plurality of terminals disposed within respective ones of the apertures, at least a portion of each of the terminals being capable of conducting an electrical current; and at least one gel element being adapted to transfer electrical current between the skin of the subject and at least one of the plurality of terminals. In one exemplary embodiment, the electrode apparatus comprises a pair of "snap" terminals disposed a predetermined distance apart within the substrate and which can be readily and positively connected to using jaw-type connectors. The electrode apparatus is adapted to mate uniformly with the skin of the subject, and maintain the desired contact with the skin as well as the predetermined spacing between the electrode terminals.

In a third aspect of the invention, an improved method of measuring the cardiac output of a living subject is disclosed. The method generally comprises: providing a plurality of electrode arrays each having a plurality of terminals, at least two of the terminals being spaced a predetermined distance apart; positioning the electrode arrays at respective locations in relation to the thoracic cavity of the subject; generating an electrical current, the current passing from a first electrode of at least one of the electrode arrays through the subject and to a second electrode of at least one of the arrays; measuring the voltage at the second electrode; determining stroke volume from the measured voltage; and determining cardiac output based at least in part on the stroke volume. In one exemplary embodiment, four electrode pairs are utilized, each having predetermined terminal spacing. The electrode pairs are placed at various locations above and below the thoracic cavity of the subject, on both sides of the cavity. Both differential voltage and cardiac rate are measured via the electrode pairs.

In a fourth aspect of the invention, a method of monitoring the electrical continuity of a plurality of electrodes in an impedance cardiography system is disclosed. The method generally comprises: providing a plurality of electrically conductive terminals; disposing the terminals in relation to the thoracic cavity of a subject; generating a current between a first of the terminals and a second of the terminals, the current passing through at least a portion of the thoracic cavity; obtaining an impedance waveform from the second terminal; and comparing the impedance waveform to a similar waveform obtained from another of the terminals; wherein the difference between the waveforms is used to evaluate the electrical continuity of the terminals.

BRIEF DESCRIPTION OF THE DRAWINGS

FIGS. 2a and 2b are perspective and cross-sectional views, respectively, of a prior art impedance cardiography electrode assembly.

DETAILED DESCRIPTION OF THE INVENTION

Reference is now made to the drawings wherein like numerals refer to like parts throughout.

It is noted that while the invention is described herein in terms of an apparatus and method for determining cardiac output suitable for use on the thorax of a human subject, the invention may also conceivably be embodied or adapted to monitor cardiac output at other locations on the human body, as well as monitoring cardiac output on other warm-blooded species. All such adaptations and alternate embodiments are considered to fall within the scope of the claims appended hereto.

Methodology

Referring now to FIGS. 3a–5, the general methodology of measuring cardiac output in a living subject according to the invention is described.

As previously discussed, the thoracic impedance $Z_T(t)$ of a living subject may be modeled as comprising a constant impedance, $Z_o$, and time-varying impedance, $\Delta Z$ (t). According to the well known "parallel-column" model of the thorax, this change in thoracic impedance, $\Delta Z$ (t), is related to the pulsatile blood volume change. In this model, illustrated in the form of a schematic diagram in FIG. 1 herein, effectively constant tissue impedances such as bone, muscle, and fat are modeled as a conducting volume $Z_o$ 102 in parallel with the pulsatile impedance of the blood $\Delta Z$ (t) 104. This second impedance 104 is a time-varying fluid column with resistivity, ρ, cylindrical length, L, and a time-varying cross-sectional area that oscillates between zero and a value A, the latter which correlates to the stroke volume V. When the pulsatile volume is at a minimum in the cardiac cycle, all the conducting tissues and fluids are represented by $Z_o$. During the cardiac cycle, the cylinder cross-sectional area increases from zero until the cylinder's volume equals the blood volume change.

Figure 4:
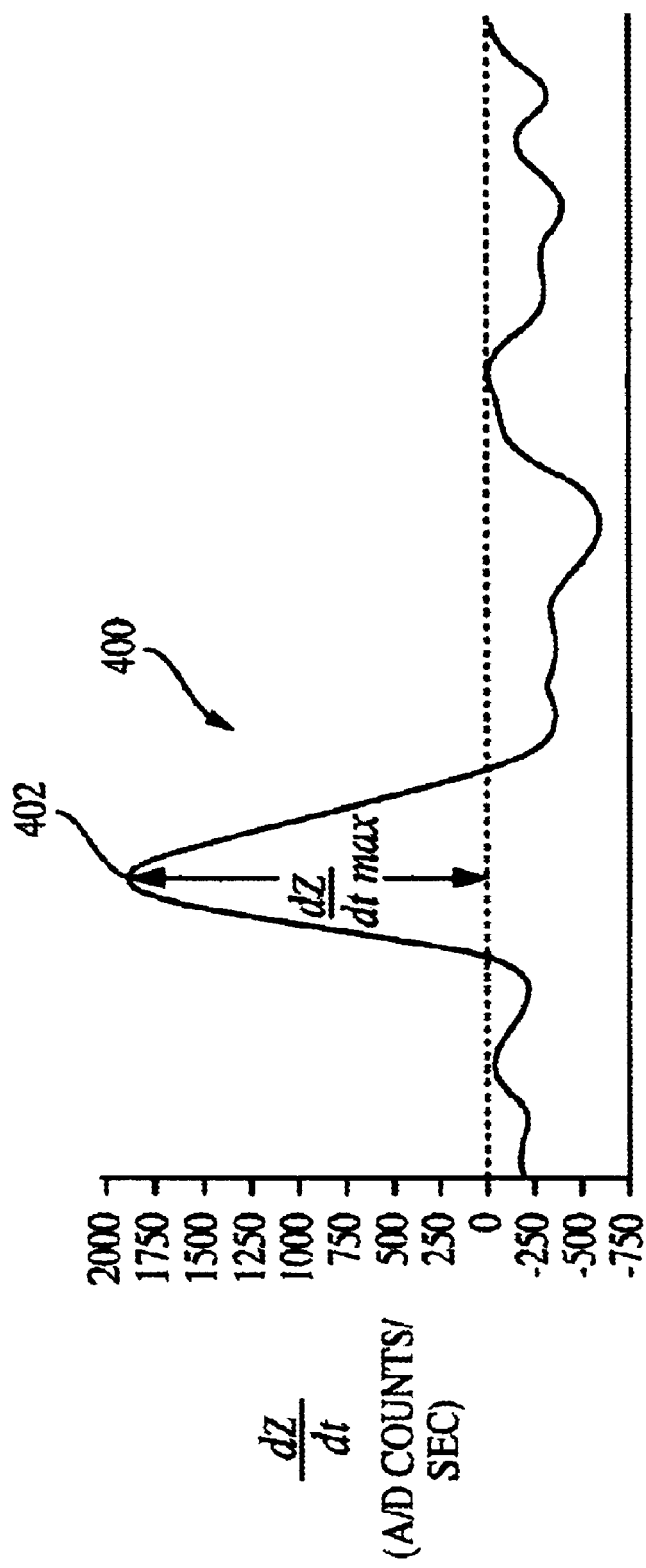
FIG. 4 is graph of the derivative of the time-variant component ΔZ (t) of thoracic impedance as a function of time, illustrating the systole "peak" used in determining ventricular ejection time (VET).

Because $Z_o$ is much greater than $\Delta Z(t)$, the relationship of Eqn. (2) holds:

$$SV = \rho \left(\frac{L^2}{Z_0^2}\right) VET \frac{dZ(t)}{dt_{min}}, \quad (2)$$

where L is the distance between the measurement electrodes in cm (FIG. 3a), VET is the ventricular ejection time in seconds, and $$\frac{dZ(t)}{dt_{min}}$$

is the magnitude of the largest negative derivative of the impedance change occurring during systole in ohms/s. Often, the impedance derivative 400 is purposely inverted as shown in FIG. 4 so that the original negative minimum change will appear as a positive maximum 402, $$\frac{dZ(t)}{dt_{max}},$$

in a manner more familiar to clinicians.

Figure 3B:
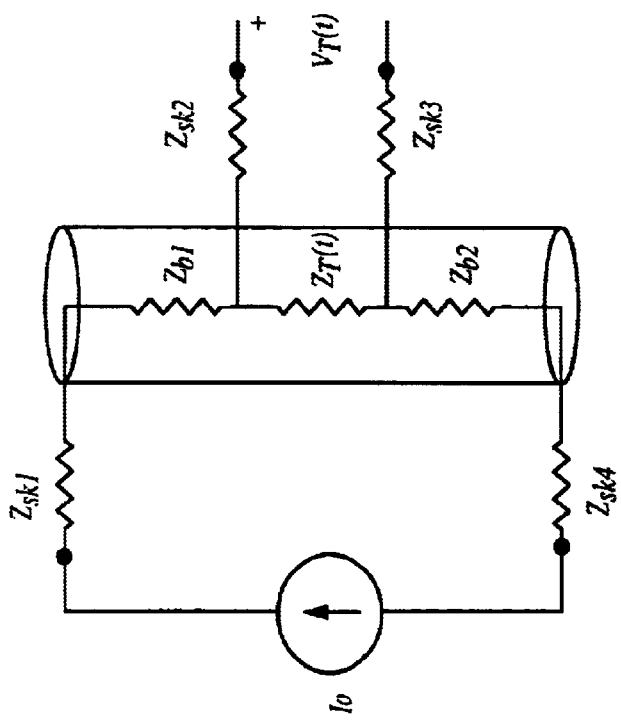
FIG. 3b is a schematic diagram illustrating the measurement of cardiac output using the electrode arrays and current source of the present invention.
Figure 3A:
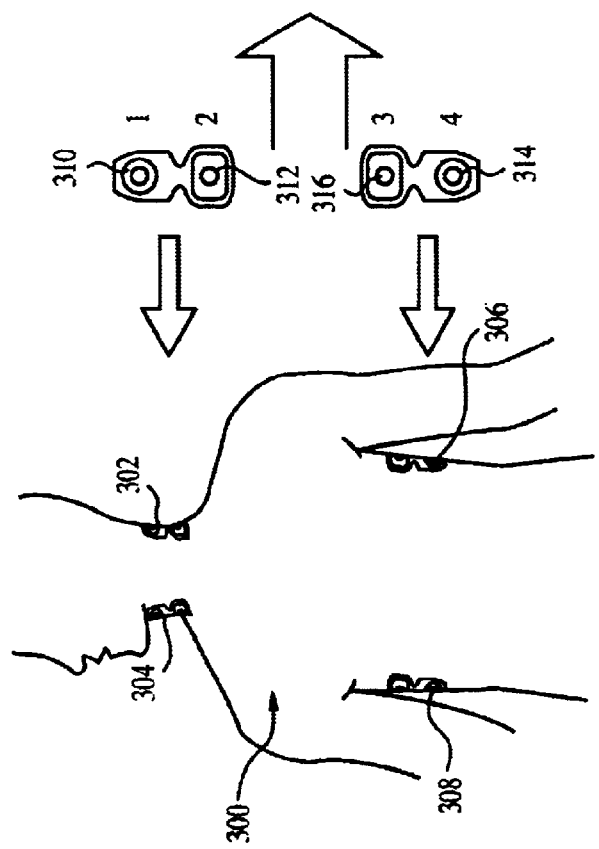
FIG. 3a is a plane view of a typical human thorax illustrating an exemplary placement of the electrode arrays of the present invention during cardiac output measurement.

The ventricular ejection time (VET) is estimated from features in the impedance waveform, which is obtained from the measurement terminals of the electrode arrays 302, 304, 306, 308 placed on various locations of the subject's thorax as illustrated in FIGS. 3a and 3b. In the present embodiment, a value of 150 ohm-cm is used for the resistivity of the blood, although it will be recognized that other values may be substituted as appropriate.

Figure 1:
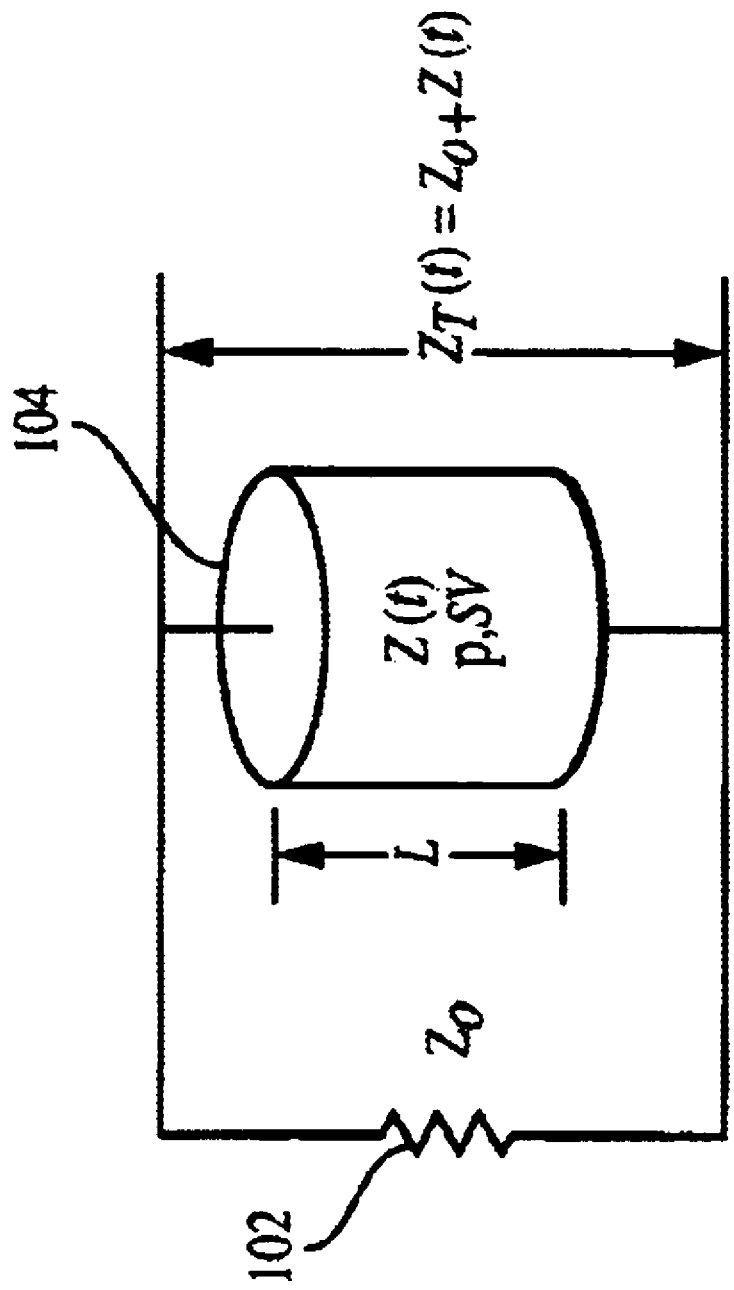
FIG. 1 is schematic diagram illustrating the parallel column model of the impedance of the thoracic cavity of a human being.

It is noted that the description of the volume of participating tissue may be modified. Rather than model the thorax as a cylinder as shown in FIG. 1 above, the thorax may instead be modeled as a truncated cone (as first described by Sramek and Bernstein). This approach results in a modified stroke volume calculation as in Eqn. (3):

$$SV = \frac{L^3}{4.25 Z_0} VET \frac{dZ(t)}{dt_{min}}. \quad (3)$$

With either of the two aforementioned approaches (i.e., cylindrical or truncated cone), the pulsatile impedance is estimated using Ohm's law, which is well known in the electrical arts. Specifically, current from a constant current source, $I_T(t)$, is applied, and the resulting voltage, $V_T(t)$, is measured in order to calculate the ratio of Eqn. (4):

$$Z_T(t) = \frac{V_T(t)}{I_T(t)}. \quad (4)$$

In the selected frequency range (i.e., 68 kHz), the typical impedance associated with a human subject's skin is 2 to 10 times the value of the underlying thoracic impedance $Z_T(t)$. To aid in eliminating the contribution from skin and tissue impedance, the present invention uses at least two, and typically four electrode arrays 302, 304, 306, 308 for measurement, as shown in FIG. 3a. The physical construction and these electrode arrays is described in detail with reference to FIGS. 7a–8 herein.

In a simple application, one electrode array 302 comprising a stimulation electrode terminal 310 and a measurement electrode terminal 312 is applied above the thorax 300 of the subject, while a second electrode array 304 (having stimulation electrode terminal 314 and measurement electrode terminal 316) is applied below the thorax 300. The AC current from the current source is supplied to the stimulation electrode terminals 310, 314. As shown in FIG. 3b, current flows from each stimulation electrode terminal 310, 314 through each constant skin impedance, $Z_{sk1}$, or $Z_{sk4}$, each constant body tissue impedance, $Z_{b1}$ or $Z_{b1}$, and each constant skin impedance, $Z_{sk2}$ or $Z_{sk3}$, to each measurement electrode terminal 312, 316. The voltages at the measurement electrode terminals 312, 316 are measured and input to a differential amplifier to obtain the differential voltage, $V_T(t)$. The desired thoracic impedance, $Z_T(t)$, is then obtained using the relationship of Eqn. (4).

As shown in FIG. 3a, two sets of electrode arrays may advantageously be used to monitor the impedance associated with the left and right portion of the thorax 300 in the present invention. When eight electrode terminals (four arrays 302, 304, 306, 308) are used in this manner, the four measurement arrays are also used to obtain an electrocardiogram (ECG), based on one of four vectors modified from Lead I, II, III, or IV. The resulting electrocardiograms are based on the original Lead configurations, but are not of diagnostic quality. Regardless of the modified Lead configuration used, the Q wave of the ECG QRS interval is used to determine the heart rate and to trigger measurements of VET within the $$\frac{dZ(t)}{dt}$$

waveform.

Figure 5:
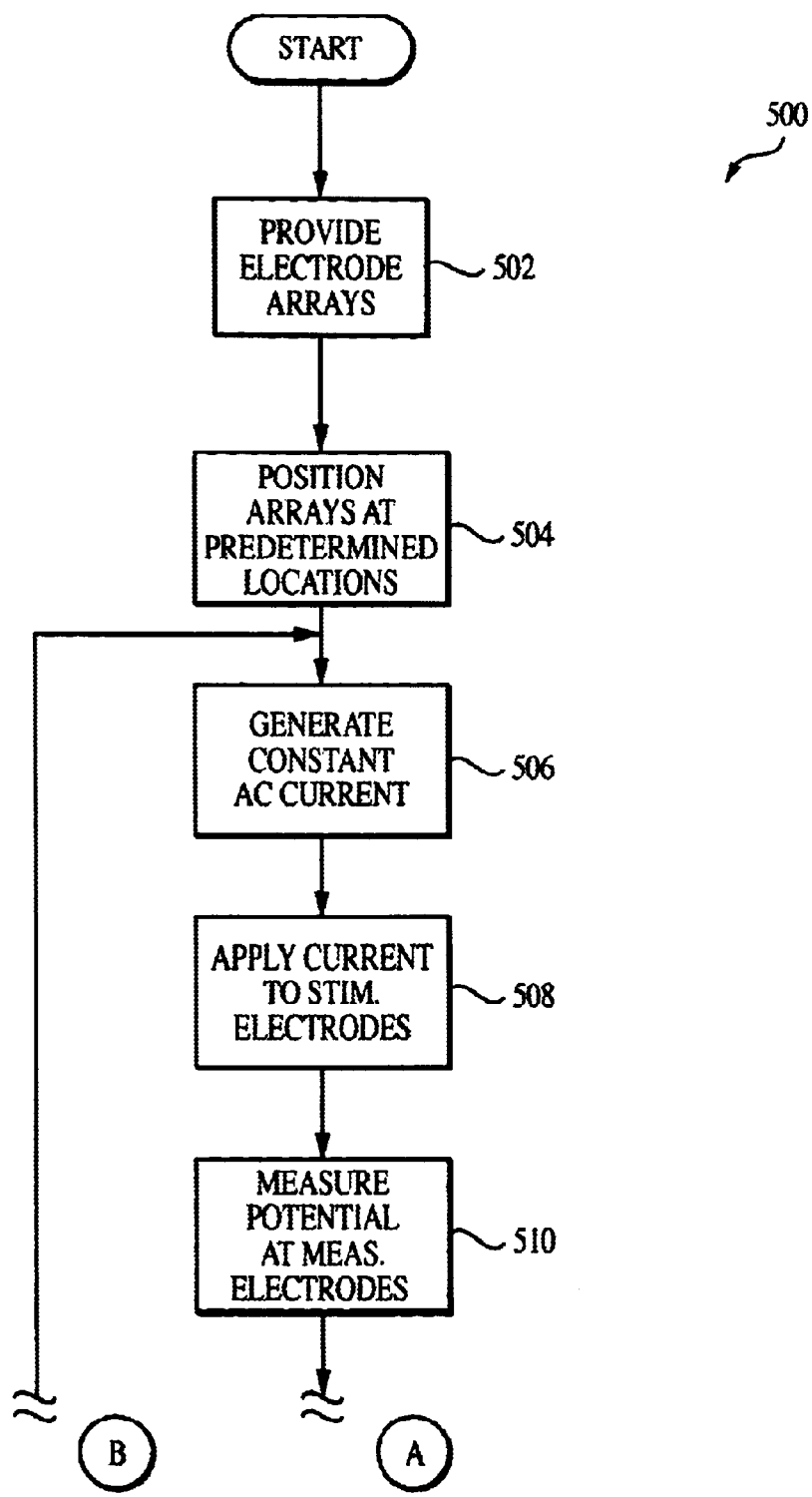
FIG. 5 is a logical flow diagram illustrating one exemplary embodiment of the method of measuring cardiac output within a living subject according to the invention.
Figure 5:
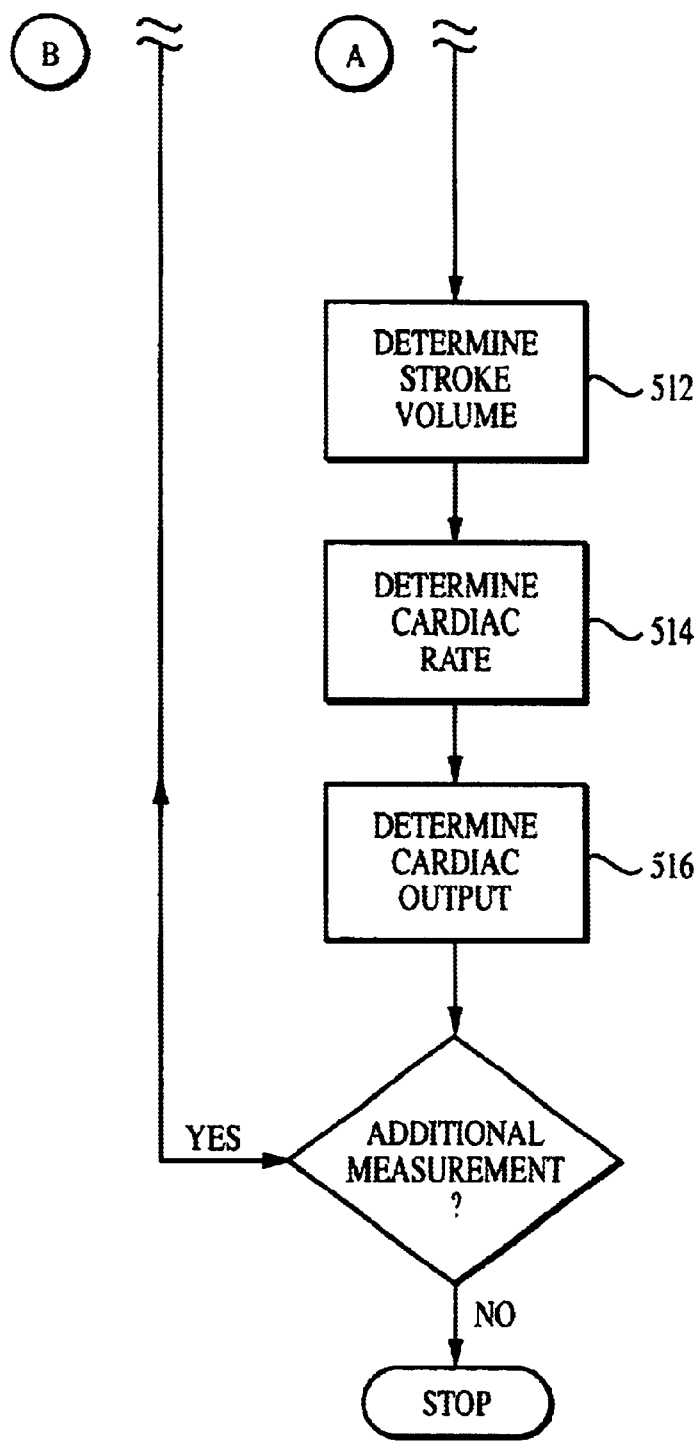

FIG. 5 illustrates the logical flow of the method of measuring cardiac output according to the invention. As shown in FIG. 5, the method 500 generally comprises first providing a plurality of electrode "arrays" of the type previously described herein per step 502. The electrode arrays are positioned at predetermined locations above and below the thoracic cavity per step 504, as illustrated in FIG. 3a herein. In one embodiment of the method, these locations are chosen to be on the right and left sides of the abdomen of the subject, and the right and left sides of the neck. These locations, with prior art band electrodes, were first used by Kubicek. Other locations and/or combinations of arrays may be substituted with equal success.

Next, a substantially constant AC current is generated in step 506, and the current applied to the stimulation electrode terminal 310, 314 of each of the electrode arrays in step 508. The voltage generated at the measurement electrode terminal 312, 316 of each electrode array is next measured in step 510. As previously discussed, this voltage is generally reduced from that applied to the stimulation electrode by virtue of the impedance of, inter alia, the thoracic cavity. Note that the measured voltage may be absolute, or relative (i.e., a differential voltage) as desired. Next, in step 512, the cardiac stroke volume from the measured voltage, using for example the relationship of Eqn. (3) above. Cardiac rate (step 514) is also determined by using the measurement electrodes to sense the ECG potentials generated by the heart of the subject. Lastly, in step 516, cardiac output is determined based on the stroke volume determined in step 512 and the cardiac rate in step 514 using the relationship of Eqn. 1 above.

Apparatus

Figure 6:
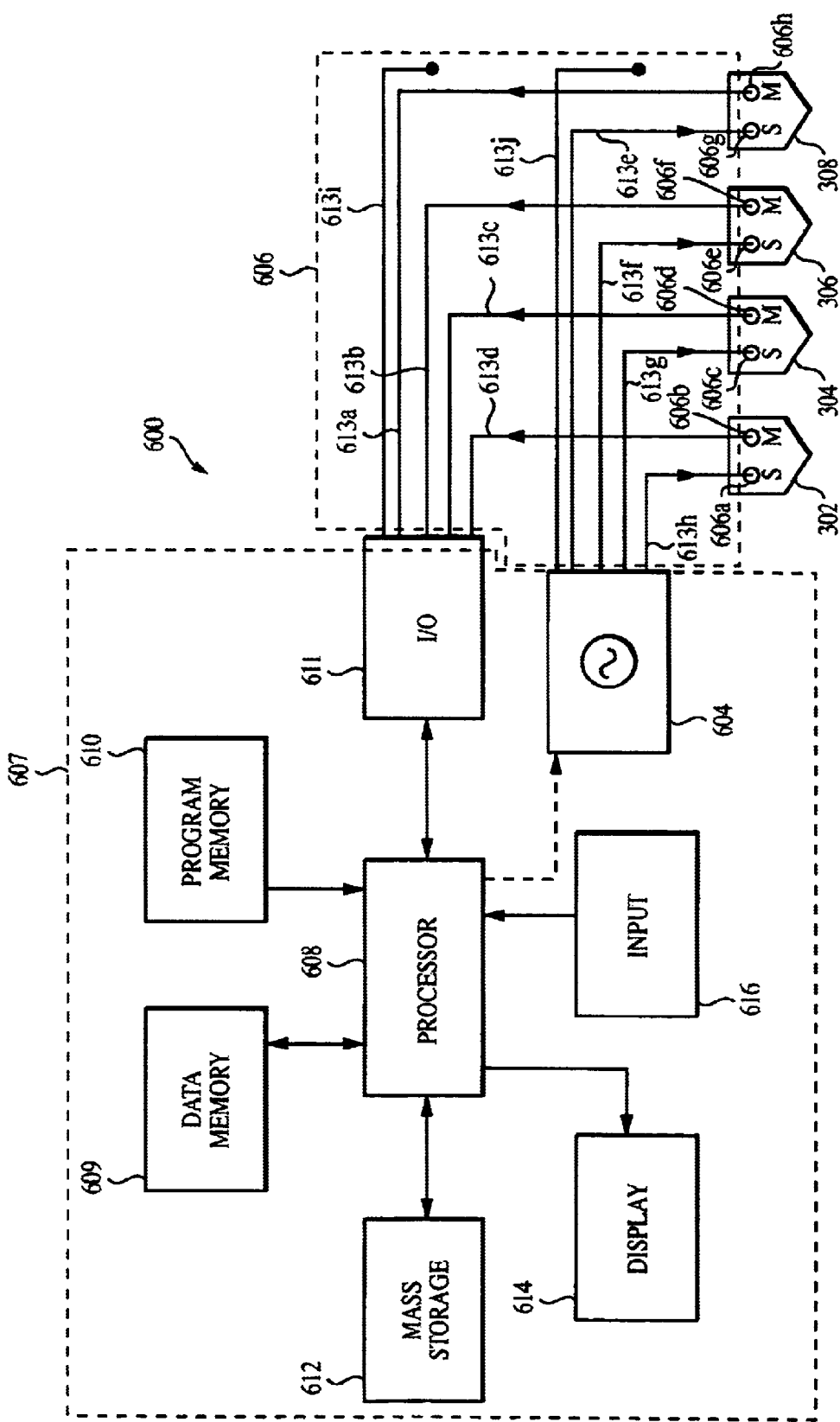
FIG. 6 is a logical block diagram illustrating one exemplary embodiment of the cardiac output measurement system of the present invention.

Referring now to FIG. 6, the apparatus for measuring cardiac output using the above-described technique is disclosed. In addition to the four electrode arrays 302, 304, 306, 308 previously discussed, the system 600 generally comprises an alternating current (AC) current source 604 capable of generating a substantially constant current, a plurality of electrical leads in the form of a multi-ended lead assembly 606 for connecting the instrument monitor 607 to the individual terminals of the electrode arrays 302, 304, 306, 308, a processor 608 with associated algorithms capable of running thereon for performing analysis of the signals measured from the measurement terminals, data and program memory 609, 610 in data communication with the processor 608 for storing and retrieving program instructions and data; an I/O interface 611 (including analog-to-digital converter) for interfacing data between the measurement electrodes and the processor 608; a mass storage device 612 in data communication with the processor for storing and retrieving data; a display device 614 (with associated display driver, not shown) for providing an output display to the system operator, and an input device 616 for receiving input from the operator. It will be recognized that the processor 608, memory 609, 610, I/O interface 611, mass storage device 612, display device 614, and input device 616 (collectively comprising the instrument monitor 607) may be embodied in any variety of forms, such as a personal computer (PC), hand-held computer, or other computing device. The construction and operation of such devices is well known in the art, and accordingly is not described further herein.

The applied current derived from the current source 604 is a 70 kHz sine wave of approximately 2.5 mA peak-to-peak. The measured voltage associated with the aforementioned sine wave is on the order of 75 mV peak-to-peak. These values are chosen to advantageously minimize electric shock hazard, although it will be appreciated that other frequencies, currents, or voltages may be substituted. The construction and operation of AC current sources is well known in the electronic arts, and accordingly is not described further herein.

The electrode lead assembly 606 of the illustrated embodiment contains a ten wire assembly (two wires are left unused) that branches to eight individual connectors 606a–h. The conductors 610a–h of the lead assembly are fashioned from electrically conductive material such as copper or aluminum, and are insulated using a polymer-based insulation having the desired dielectric strength as is well known in the electrical arts. The length of the conductors may also be controlled so as to match the impedance of each individual conductor to that of the others within the assembly 606.

Using one of four modified Lead configurations, the body surface potential is measured between two measurement electrodes. This time-varying voltage reflects the electrical activity of the heart, and contains one QRS interval per cardiac cycle. The biopotential is analyzed to identify each QRS complex. The frequency of QRS complexes determines the heart rate. The Q wave within the QRS complex is then used to trigger identification of VET within the $$\frac{dZ(t)}{dt}$$

waveform, as the opening of the aortic valve (the beginning of VET) occurs after the appearance of the Q wave.

Figure 7A:
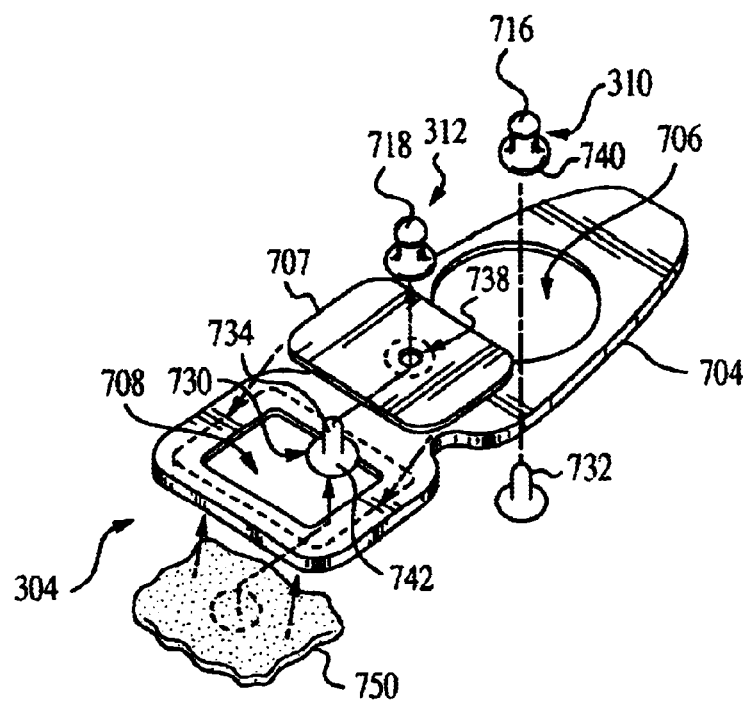
FIG. 7a is an assembly diagram illustrating the construction of a first embodiment of the electrode array of the present invention.
Figure 7B:
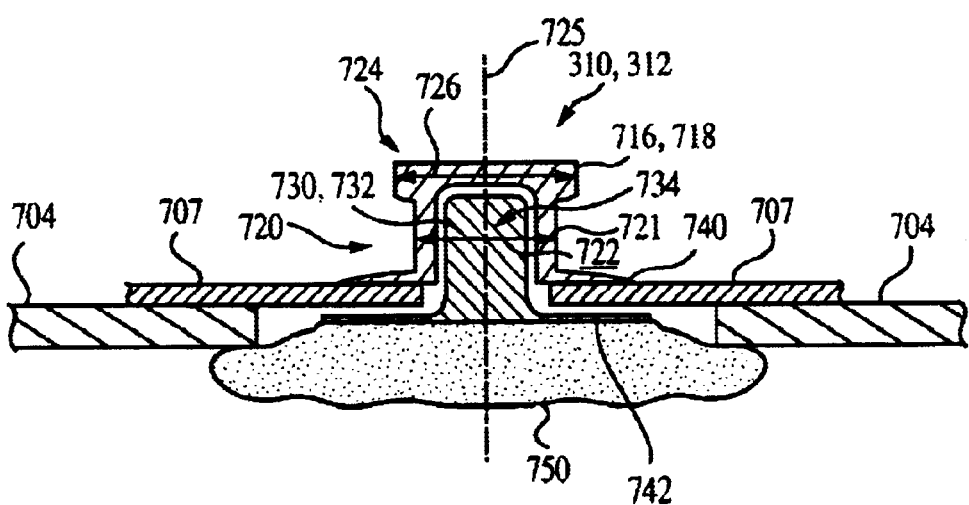
FIG. 7b is a cross-sectional view detailing the shape of the electrode terminals of the electrode array of FIG. 7a, and the construction thereof.
Figure 7D:
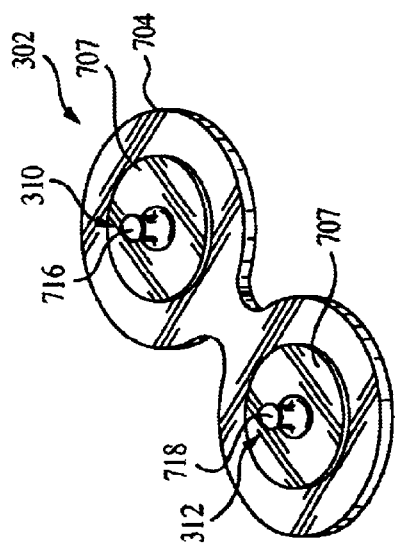
FIG. 7d is a perspective view of a second embodiment of the electrode array of the invention.
Figure 7C:
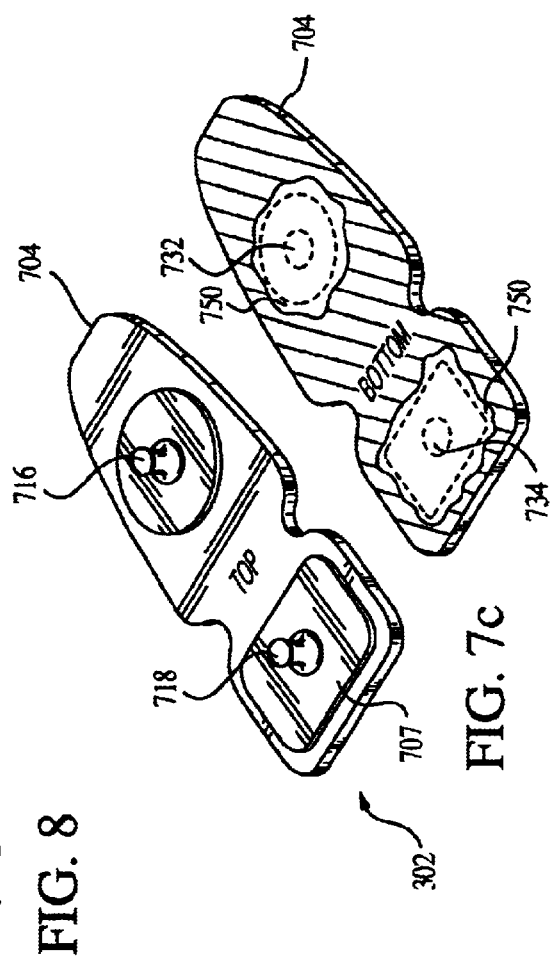
FIG. 7c illustrates top and bottom perspective views of the electrode array of FIG. 7a when fully assembled.

Referring now to FIGS. 7a–7c, the electrode arrays 302, 304, 306, 308 of the invention are described in detail. As illustrated in FIG. 7a, each array comprises a flexible substrate 704 having a plurality of apertures 706, 708 formed therein. In the illustrated embodiment, two terminals 310, 312 are disposed through the apertures such that the top portions 716, 718 of the terminals project above the plane of the substrate 704. The two terminals 310, 312 comprise a stimulation terminal 310 and measurement terminal 312 as previously described with respect to FIG. 3a. The stimulation terminal 310 is used to apply the potential necessary to generate the current flowing through the thoracic cavity of the subject. It will be noted that despite designation of one terminal as a "stimulation terminal" and one as a "measurement" terminal, the role of these terminals may be reversed if desired, since they are functionally and physically identical but for the potential applied thereto (or measured therefrom). It is noted that the asymmetric shape of the substrate 704 of the embodiment of FIGS. 7a–7c may be used to assist the clinician in rapidly determing which electrode is the stimulation electrode and which the measurement electrode, such as by assigning a convention that the end of the array having a given shape always contains the stimulation electrode. Additionally, the substrate may be shaped to adapt to certain physical features of the patient, such as by using a substrate having a broader width so as to better conform to the generally cylindrical shape of the subject's neck. Any number of different substrate shapes may be employed; FIG. 7d illustrates one such alternative shape.

As shown in FIGS. 7a–7c, The terminals 310, 312 are firmly held in place within the substrate 704 at a predetermined distance 705 by a mounting element 707 or any one of a variety of other constructions as will be described in greater detail below. The distance (measured centerline-to-centerline on the terminals 310, 312) is approximately 5 cm in the embodiment of FIG. 7a, although it will be recognized that other distances may be substituted. Desired distances may be determined through experimentation, anecdotal observations, calculations, or any other suitable method; however, experimental evidence obtained by the Applicant herein indicates that a distance of 5 cm is optimal for impedance cardiography measurements.

The substrate 704 in the embodiment of FIG. 7a is formed from a Polyethylene foam, although other materials such as cloth or vinyl may be substituted. The polyethylene foam is chosen for its compliance and flexibility, thereby allowing it to conform somewhat to the contours of the subject's anatomy, while still maintaining sufficient rigidity for maintaining the terminals 312, 314 in the desired position and orientation.

As shown in FIG. 7b, the terminals 310, 312 of each array comprise a generally cylindrical shaped sidewall portion 720 having a first diameter 722, and a top portion 724 having a second diameter 726, the second diameter 726 being greater than the first diameter 722 in order to assist in retaining a connector mated to the terminal 310, 312 as described in greater detail below. The outer wall 721 of the sidewall portion 720 is essentially vertical in orientation (i.e., parallel to the central axis 725 of the terminal 310, 312), while the top portion is progressively rounded as shown. The terminals may be manufactured from an extruded metal such nickel, with a coating of brass, or may be molded from carbon. Alternatively, the terminals may be molded of plastic, and coated with a metal such as gold or impregnated with carbon. The extruded metal possesses the advantage of low cost, while the molded plastic impregnated with carbon possesses the advantage of radiolucency. A terminal molded of plastic and coated with gold may possess low noise artifact.

The terminals 310, 312 of the electrode array comprise a two piece construction, having an upper terminal element 730 and a lower terminal element 732 as shown in FIGS. 7a and 7b. The post 734 of the lower terminal element 732 is adapted to be frictionally received within the cavity 736 of the upper terminal element when the two components are mated. In this fashion, the upper and lower elements 730, 732 form a single unit when assembled, with the mounting element 707 being frictionally held or "pinched" between the lower surface 740 of the upper element 730 and the upper surface 742 of the lower element 732. The post 734 of the lower element perforates the mounting element 707, or alternatively penetrates through a pre-existing aperture 738 formed therein. The lower elements 730, 732 of the electrode array terminals 310, 312 are coated with Ag/AgCl, although other materials with the desirable mechanical and electrochemical properties such as Zinc Chloride may be used if desired.

The electrolytic element 750 of each electrode array comprises an electrolytic gel of the type well known in the bio-electrical arts; in the present embodiment, the gel comprises an ultraviolet (UV) cured potassium chloride (KCl) gel, although it will be recognized that other types of compounds or materials may be used. UV curing of the gel allows the element 750 to have a more solidified consistency and improved mechanical properties, thereby preventing excessive spreading or thinning of the element when the array is applied to the subject while still maintaining its overall adhesiveness and electrolytic properties. As shown in FIGS. 7b and 7c, the element 750 is sized so as to encompass the edges 752 of the respective aperture 706, 708 in the substrate 704 over which it is placed when assembled, although other configurations may be used. The top portion 755 of the element 750 fits at least partially within the aperture 706, 708 and conforms substantially thereto, thereby effecting contact with the bottom surface 760 of the bottom terminal element 732. In this way, ions are passed between the skin of the subject and the terminals of the array via the gel element 750. The gel also provides for adhesion of the array to the skin of the subject, although the array of the present embodiment also includes a separate adhesive 762 which is applied to the bottom surface of the substrate 704, as shown in FIG. 7c.

Since the placement of the electrolytic element 750 with respect to the terminals 310, 312 of the array may in certain cases affect the ultimate measurements of cardiac output obtained with the system, the gel of the element 750 is advantageously placed in the embodiment of FIGS. 7a–c so as to be symmetric with respect to the terminal 310, 312. It will be recognized, however, that the element(s) 750 may also be placed so as to produce certain desired electrolytic conditions. Similarly, the element 750 may be split into two or more component parts if desired.

Figure 8:
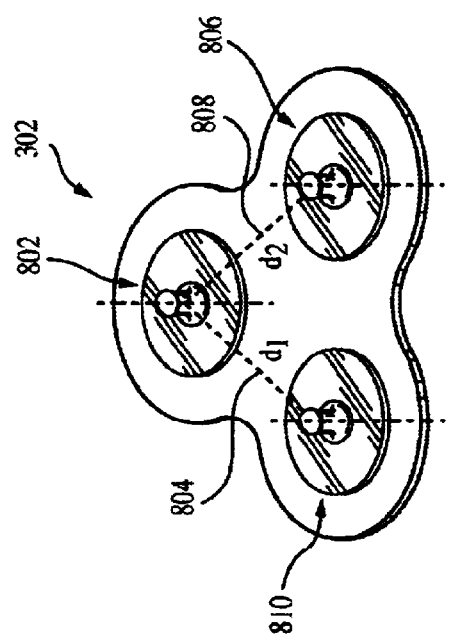
FIG. 8 is a perspective view of a third embodiment of the electrode array of the invention.

Furthermore, it is noted that while the embodiment of FIGS. 7a–c employs two fixed terminals that are effectively immovable within the substrate, means for allowing adjustment or change of the relative position of the terminals may be substituted. For example, as illustrated in FIG. 8, a terminal array having three terminal posts may be used, the second post 802 being spaced a first distance 804 from the first post 806, and the third post 810 being spaced a second distance 808 from the first post 806, such that the clinician can select one of two terminal spacings as desired.

Figure 9:
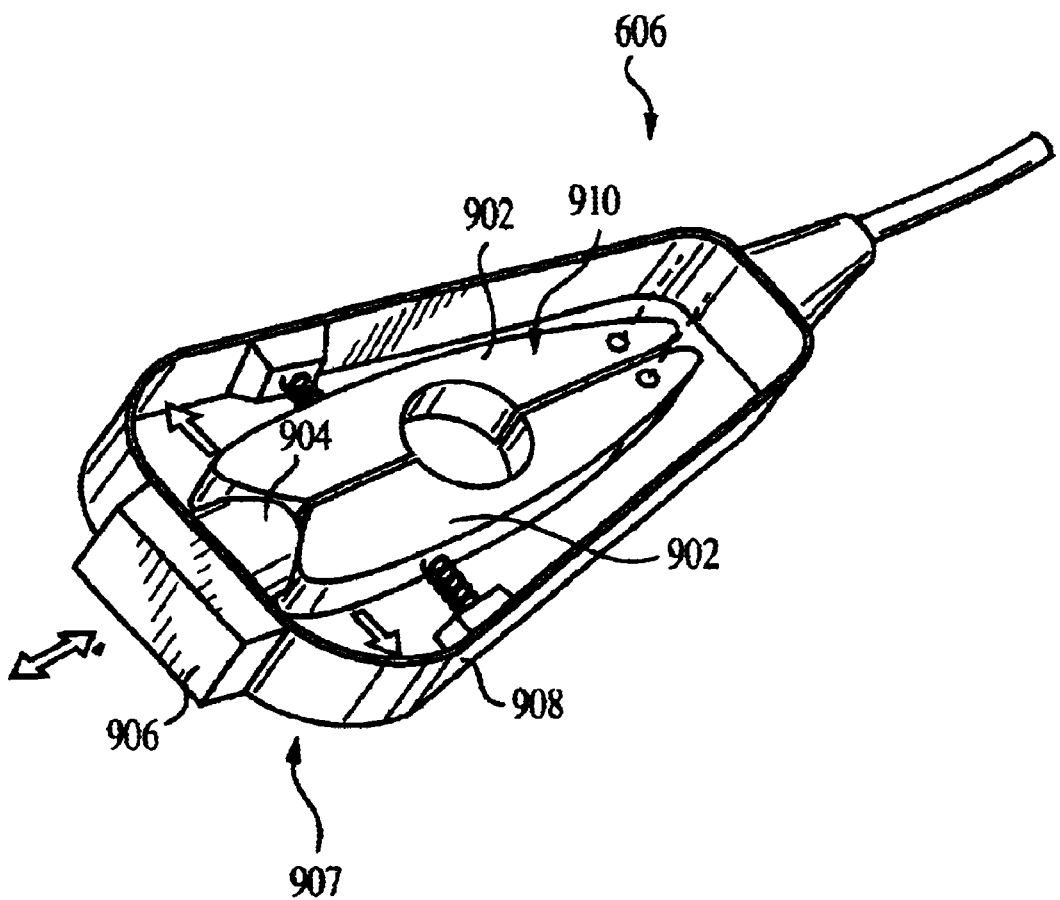
FIG. 9 is perspective view of one embodiment of a biased-jaw electrical connector as used in conjunction with the present invention.

As illustrated in FIG. 9, each electrode lead assembly connector 606a–h is designed to mitigate the downward force required to mate the connector with its respective electrode array terminal. Specifically, each connector 606a–h contains two spring-biased conductive jaws 902 that are spread apart by the cam surface 904 of an actuator button 906 disposed on the front 907 of the connector body 908. The connector jaws 902 and bias mechanism are designed to allow the upper and sidewall portions 724, 720 of the electrode terminal 310, 312 (FIG. 7b) to be received within the recess 910 of the jaws 902 when the button 906 is fully depressed. In this fashion, effectively no downward force is required to engage the connector to its respective terminal. The jaws 902 are contoured to engage substantially the entire surface of the sidewall portion 720 of the terminal when the actuator button 906 is released. Since the sidewall portion 720 of the terminal is effectively circular in cross-section, the connector may advantageously rotate around the axis of the terminal 310, 312 when lateral tension is applied to the conductor attached to that connector. U.S. Pat. No. 5,895,298 issued Apr. 20, 1999, entitled "DC Biopotential Electrode Connector and Connector Condition Sensor," and incorporated herein by reference in its entirety, describes a bias jaw electrical connector of the type referenced above in greater detail.

When used with the four two-terminal electrode arrays 302, 304, 306, 308 shown in FIG. 3a, each connector 606a–h is fastened to one of the two terminals 310, 312 of an electrode array. The 68 kHz constant current is applied from the current source to four electrode terminals (i.e., one terminal per array). Hence, complete circuits are formed between the current source and the I/O device 611 of the system 600 via the electrical conductors and connectors associated with the stimulation electrode terminals, the stimulation electrode terminals themselves, the thorax of the subject, the measurement terminals, and the electrical conductors and connectors associated with the measurement terminals.

Method of Evaluating Electrical Continuity

Figure 10:
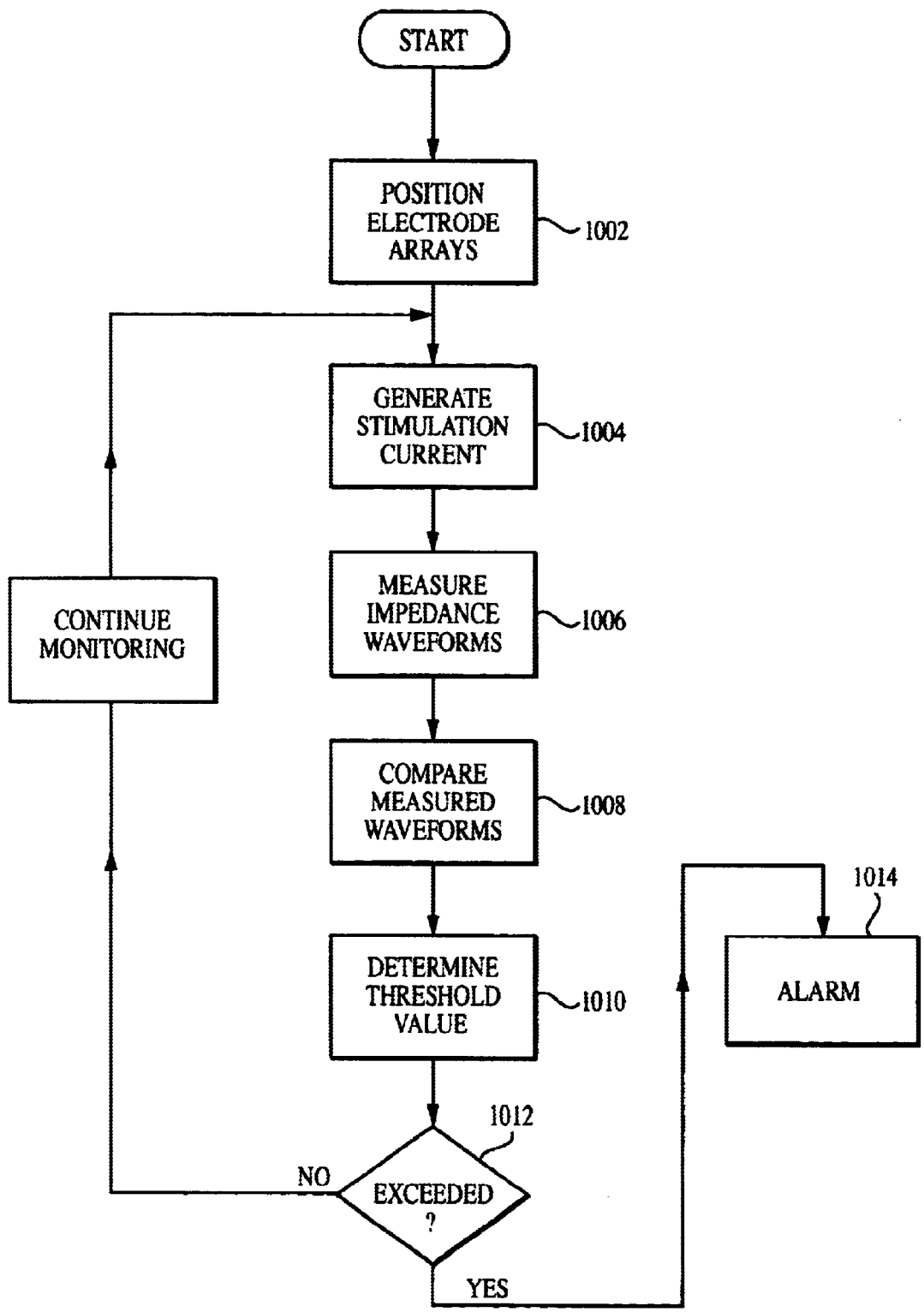
FIG. 10 is a logical flow diagram illustrating one exemplary embodiment of the method of evaluating electrical lead continuity according to the invention.

Referring now to FIG. 10, the method of evaluating the electrical continuity of one or more leads within the system is described. Note that while the following description is based on the two-terminal array configuration (FIGS. 7a–7c) and the use of four arrays as shown in FIG. 3a, the method may be applied to many alternate configurations with equal success.

First, in step 1002, the electrode arrays are disposed on the skin of the subject. The position at which the electrode arrays are disposed on the subject are measured in relation to the thoracic cavity as illustrated in FIG. 3a, or alternatively may be inferred by the weight and height of the subject. Next, a current is generated between the stimulation electrodes and the measurement electrodes of the respective arrays in step 1004. As previously discussed, the current passes through at least a portion of the subject's thoracic cavity, encountering a time-variant impedance therein.

An impedance waveform is then measured from two or more of the measurement terminals of the arrays in step 1006. The waveforms comprise measurements of impedance as a function of time, which is well known in the cardiographic arts. These measured waveforms are then compared to one another in step 1008 to detect changes or variations between them. In the present embodiment, two waveforms are differenced by way of a simple differencing algorithm resident on the processor 608 of the system 600 (FIG. 6), although it will be recognized that other approaches may be used. For example, the base impedance may be calculated for the left and right sides. The larger base impedance may then be subtracted from the smaller base impedance, with this difference then divided by the smaller impedance. The resulting percentage ratio, when greater than a predetermined threshold value, may represent the presence of detached or loose electrodes. While some variation between the waveforms is normal, significant variations are indicative of either a degraded electrical connection, such as between the electrode array terminal and its respective connector, or between the electrolytic gel and the skin of the patient, or even the gel and the terminal of the array or between the cable and connector. A threshold value is determined and set by the operator of the system in step 1010 such that when the threshold "difference" is exceeded as determined by the aforementioned algorithm (step 1012), the operator will be alerted to the degraded condition such as by a visual or audible alarm in step 1014.

It is noted that the use of the multi- terminal electrode arrays having predetermined and substantially equal terminal spacing as previously described allows such comparisons between electrode waveforms to be made; errors resulting from uncontrolled spacing of the terminals are effectively eliminated. Using prior art electrodes, the aforementioned method would be largely ineffective, since these error sources would force the threshold value to be set artificially high, thereby potentially masking conditions of degraded electrical continuity which could affect the ultimate accuracy of and cardiac output estimation made by the system.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A system for determining the cardiac output of a living subject comprising:
    a plurality of electrode assemblies, each electrode assembly having a plurality of terminals, at least two of said plurality of terminals being spaced from one another by a predetermined distance;
    a current source capable of generating a substantially constant current;
    a plurality of electrical leads connecting said current source with individual ones of said terminals of said electrode assemblies,
    a circuit for measuring the difference in voltage at said terminals resulting from the flow of said current through said subject and said terminals under varying cardiac conditions of said subject; and
    a circuit for measuring ECG potentials from at least one of said electrode assemblies.

2. The system of claim 1, further comprising a circuit for measuring the difference in the impedance of at least two of said terminals as a function of time, said difference being compared to a first value to evaluate the electrical continuity of at least one of said terminals, said first value being based at least in part on said predetermined distance.

3. The system of claim 1, wherein said electrode assemblies comprise:
    a substrate, said substrate having a plurality of apertures formed therein;
    a plurality of terminals disposed within respective ones of said apertures, at least a portion of each of said terminals being capable of conducting an electrical current; and
    at least one gel element, said at least one gel element adapted to transfer electrical current between the skin of said subject and said at least two of said plurality of terminals.

4. The system of claim 3, wherein said circuit for measuring ECG potentials comprises a circuit adapted to measure body surface potentials between at least two of said terminals in order to identify a plurality of QRS complex events within said subject.

5. The system of claim 4, further comprising a processor in data communication with both said circuit for measuring the difference in voltage and said circuit for measuring ECG potentials, said processor being adapted to determine cardiac output based on said difference in voltage and said QRS complex events.

6. The system of claim 3, wherein said terminals each comprise:
    a central axis;
    a sidewall portion substantially parallel to said axis; and
    a top portion, said top portion having a diameter greater of that of said vertical sidewall portion.

7. The system of claim 6, wherein said electrical leads each comprise a connector, said connector being adapted to form an electrical conduction path between said connector and a respective one of said terminals, said connector further comprising a plurality of electrically conductive arms biased against said sidewall portion of said terminal when said connector is mated with said terminal.

8. A method of measuring the cardiac output of a living subject, comprising:
    providing a plurality of electrode arrays, each of said electrode arrays having a plurality of terminals, at least two of said terminals being spaced a predetermined distance apart;
    positioning the electrode arrays at respective locations in relation to the thoracic cavity of the subject;
    generating an electrical current, said current passing from a first electrode of at least one of said electrode arrays through said subject and to a second electrode of at least one of said arrays;
    measuring the voltage at said second electrode of said at least one electrode array;
    determining stroke volume from the measured voltage; and
    determining cardiac output based at least in part on said stroke volume.

9. The method of claim 8, wherein the act of positioning comprises placing at least one electrode array on both the left and right sides of the subject's abdomen.

10. The method of claim 9, further comprising placing at least one electrode array on both the left and right sides of the subject's neck.

11. The method of claim 8, wherein the act of determining stroke volume comprises determining ventricular ejection time (VET) and the derivative of impedance, and calculating stroke volume based at least in part thereon.

12. The method of claim 11, wherein the act of determining cardiac output comprises multiplying stroke volume and cardiac rate.

13. The method of claim 12, further comprising:
    measuring ECG potentials from said subject using at least one of said electrode arrays; and
    determining cardiac rate based at least in part on said ECG potentials.

14. The method of claim 8, wherein the act of measuring voltage comprises measuring a differential voltage across respective ones of the terminals of at least one of said electrode arrays.

15. The method of claim 8, further comprising:
    measuring a first impedance waveform at a first of said terminals;
    measuring a second impedance waveform at a second of said terminals; and
    evaluating the continuity of at least one electrical connection based at least in part on the relationship of at least one of said first and second impedance waveforms to a predetermined value.

16. The method of claim 15, wherein the act of evaluating comprises taking the difference of said first and second waveforms and comparing that difference to a threshold value.

17. A cardiac electrode assembly for use on a living subject, comprising:
    a substrate, said substrate having a plurality of apertures formed therein, at least two of said apertures being formed a predetermined distance apart;
    a plurality of terminals disposed within respective ones of said apertures, at least a portion of each of said terminals being capable of conducting an electrical current; and
    at least one gel element, said at least one gel element being adapted to transfer electrical current between the skin of said subject and at least one of said plurality of terminals.

18. The electrode assembly of claim 17, wherein said terminals each comprise a substantially vertical sidewall portion, and a top portion having a diameter greater of that of said vertical sidewall portion so as to retain an electrical connector attached thereto.

19. The electrode assembly of claim 17, wherein said predetermined distance is established such that differential voltage measurements taken across said terminals fall within a predetermined voltage band when electrical continuity exists in each of said terminals.

20. A cardiac electrode assembly adapted for measuring the cardiac output of a living subject, comprising:
    a flexible substrate, said substrate having at least two apertures formed therein, said at least two apertures being formed a predetermined distance apart;
    at least two terminals disposed within respective ones of said apertures, at least a portion of each of said terminals being capable of conducting an electrical current; and
    a first electrolytic element disposed proximate to a first of said at least two apertures, said first electrolytic element adapted to transfer an electrical potential between the skin of said subject and a first of said at least two terminals;
    a second electrolytic element disposed proximate to a second of said at least two apertures, said second electrolytic element adapted to transfer an electrical potential between the skin of said subject and a second of said at least two terminals;
    an attachment element, said attachment element cooperating with said substrate and the skin of said living subject to removably affix said electrode assembly to said skin.

21. A method of monitoring the electrical continuity of a plurality of electrodes in an impedance cardiography system, comprising:
    providing a plurality of electrically conductive terminals;
    disposing the terminals in relation to the thoracic cavity of a subject;
    generating a current between a first of said terminals and a second of said terminals, said current passing through at least a portion of said thoracic cavity;
    obtaining an impedance waveform from said second terminal; and
    comparing said impedance waveform to a similar waveform obtained from another of said terminals;
    wherein the difference between said impedance waveform and said similar waveform is d to evaluate the electrical continuity of said first terminal.

22. A system for determining the cardiac output of a living subject, comprising:
    a plurality of electrode assemblies, each electrode assembly having:
        a substrate having a plurality of apertures formed therein;
        a plurality of electrically conductive terminals disposed within respective ones of said apertures, each terminal having a central axis, a sidewall portion substantially parallel to said axis, and a top portion, said top portion having a diameter greater of that of said vertical sidewall portion, at least two of said plurality of terminals being spaced from one another by a predetermined distance; and
        at least one gel element, said at least one gel element adapted to transfer electrical current between the skin of said subject and said at least two of said plurality of terminals;
    a current source capable of generating a substantially constant current;
    a plurality of electrical leads connecting said current source with individual ones of said terminals of said electrode assemblies, said electrical leads each comprising a connector, said connector being adapted to form an electrical conduction path between said connector and a respective one of said terminals, said connector further comprising a plurality of electrically conductive arms biased against said sidewall portion of said terminal when said connector is mated with said terminal;
    a circuit for measuring the difference in voltage at said terminals resulting from the flow of said current through said subject and said terminals under varying cardiac conditions of said subject; and
    a circuit for measuring ECG potentials from at least one of said electrode assemblies.

23. The system of claim 22, further comprising a circuit for measuring the difference in the impedance of at least two of said terminals as a function of time, said difference being compared to a first value to evaluate the electrical continuity of at least one of said terminals, said first value being based at least in part on said predetermined distance.

24. The system of claim 22, wherein said circuit for measuring ECG potentials comprises a circuit adapted to measure body surface potentials between at least two of said terminals in order to identify a plurality of QRS complex events within said subject.

25. The system of claim 24, further comprising a processor in data communication with both said circuit for measuring the difference in voltage and said circuit for measuring ECG potentials, said processor being adapted to determine cardiac output based on said difference in voltage and said QRS complex events.

26. A system for determining the cardiac output of a living subject, comprising:
  a plurality of electrode assemblies, each electrode assembly having a plurality of terminals, at least two of said plurality of terminals being spaced from one another by a predetermined distance;
  a current source capable of generating a substantially constant current;
  a plurality of electrical leads connecting said current source with individual ones of said terminals of said electrode assemblies,
  a circuit for measuring the difference in voltage at said terminals resulting from the flow of said current through said subject and said terminals under varying cardiac conditions of said subject; and
  a circuit for measuring ECG potentials from at least one of said electrode assemblies;
wherein at least a first portion of said plurality of electrode assemblies are adapted for placement on the neck of said subject; and a second portion of said plurality of electrode assemblies are adapted for placement at or near the level of the xiphoid process of said subject.

27. A method of measuring the cardiac output of a living subject, comprising:
  providing a plurality of electrode arrays, each of said electrode arrays having a plurality of terminals, at least two of said terminals being spaced a predetermined distance apart;
  positioning the electrode arrays at respective locations on the neck and thorax xiphoid process of the subject;
  generating an electrical current, said current passing from a first electrode of at least one of said electrode arrays through said subject and to a second electrode of at least one of said arrays;
  measuring the voltage at said second electrode of said at least one electrode array;
  determining stroke volume from the measured voltage; and
  determining cardiac output based at least in part on said stroke volume.

28. A method of monitoring the electrical continuity of a plurality of electrodes in an impedance cardiography system, comprising:
  providing a plurality of electrically conductive terminals;
  disposing the terminals in relation to the thoracic cavity of a subject;
  generating a current between a first of said terminals and a second of said terminals, said current passing through at least a portion of said thoracic cavity;
  obtaining a first impedance waveform from said second terminal; and
  comparing said first impedance waveform to a threshold value;
  wherein the difference between said first impedance waveform and said threshold impedance value is used to evaluate the electrical continuity of said first terminal.

29. The method of claim 28, wherein said threshold value is determined by:
  obtaining a second impedance waveform from at least one of said electrically conductive terminals prior to said act of obtaining said first impedance waveform;
  storing at least a portion of said second waveform in a storage device; and
  determining said threshold based at least in part on said stored at least portion of said second waveform.

30. The method of claim 28, wherein said threshold value is determined by:
  applying a constant current between said first and second electrodes;
  obtaining a voltage value from at least one of said terminals; and
  deriving said threshold impedance value using at least said voltage value and said constant current.

31. A method of monitoring the electrical continuity of a plurality of electrodes in an impedance cardiography system, comprising:
  providing a plurality of electrically conductive terminals;
  disposing respective ones of the terminals at the neck and approximately the level of the xiphoid process of the thorax of a subject, at least two of said terminals being disposed at predetermined spacing with respect to each other;
  generating a current between a first of said terminals and a second of said at least two terminals, said current passing through at least a portion of said thoracic cavity;
  obtaining a first impedance waveform from said second terminal; and
  comparing said first impedance waveform to a threshold value;
  wherein the difference between said first impedance waveform and said threshold impedance value is used to evaluate the electrical continuity of said first terminal.

32. The method of claim 31, wherein said threshold value is determined by:
  obtaining a second impedance waveform from at least one of said electrically conductive terminals prior to said act of obtaining said first impedance waveform;
  storing at least a portion of said second waveform in a storage device; and
  determining said threshold based at least in part on said stored at least portion of said second waveform.

* * * * *

UNITED STATES PATENT AND TRADEMARK OFFICE
CERTIFICATE OF CORRECTION

PATENT NO.    : 6,636,754 B1                                              Page 1 of 1
DATED         : October 21, 2003
INVENTOR(S)   : Gail D. Baura and James O. Elf It is certified that error appears in the above-identified patent and that said Letters Patent is hereby corrected as shown below:

<u>Column 14,</u>
Lines 21-23, "wherein the difference between said impedance waveform and said similar waveform is d to evaluate the electrical continuity of said first terminal."
Should read:
-- wherein the difference between said impedance waveform and said similar waveform is used to evaluate the electrical continuity of said first terminal. --

Signed and Sealed this

Thirteenth Day of January, 2004

JON W. DUDAS
*Acting Director of the United States Patent and Trademark Office*